US007632652B2

(12) United States Patent
Bieniarz et al.

(10) Patent No.: US 7,632,652 B2
(45) Date of Patent: Dec. 15, 2009

(54) ENZYME-CATALYZED METAL DEPOSITION FOR THE ENHANCED IN SITU DETECTION OF IMMUNOHISTOCHEMICAL EPITOPES AND NUCLEIC ACID SEQUENCES

(75) Inventors: Christopher Bieniarz, Tucson, AZ (US); Casey A. Kernag, Tucson, AZ (US); Jerome W. Kosmeder, Tucson, AZ (US); Paula Rodgers, Tucson, AZ (US); Jennifer Wong, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 726 days.

(21) Appl. No.: 10/877,919

(22) Filed: Jun. 24, 2004

(65) Prior Publication Data

US 2004/0265922 A1 Dec. 30, 2004

Related U.S. Application Data

(60) Provisional application No. 60/482,596, filed on Jun. 24, 2003.

(51) Int. Cl.
C12Q 1/42 (2006.01)
C12Q 1/44 (2006.01)
C12Q 1/54 (2006.01)
C12Q 1/68 (2006.01)
G01N 33/53 (2006.01)
G01N 33/543 (2006.01)
G01N 33/567 (2006.01)

(52) U.S. Cl. ............................ 435/7.91; 435/6; 435/7.1; 435/14; 435/19; 435/21; 435/40.5; 435/40.52; 435/188; 436/503; 436/518; 436/164; 549/218; 549/398; 558/190

(58) Field of Classification Search .................. 435/7.1, 435/7.91, 19, 21, 40.5, 40.52, 6, 14, 188; 436/503, 518, 164
See application file for complete search history.

(56) References Cited

U.S. PATENT DOCUMENTS

| 5,073,483 A | 12/1991 | Lebacq |
| 5,116,734 A | 5/1992 | Higgs et al. |
| 5,143,854 A | 9/1992 | Pirrung et al. |
| 5,252,743 A | 10/1993 | Barrett et al. |
| 5,355,439 A | 10/1994 | Bernstein et al. |
| 5,384,261 A | 1/1995 | Winkler et al. |
| 5,412,087 A | 5/1995 | McGall et al. |
| 5,424,186 A | 6/1995 | Fodor et al. |
| 5,445,934 A | 8/1995 | Fodor et al. |
| 5,451,683 A | 9/1995 | Barrett et al. |
| 5,510,270 A | 4/1996 | Fodor et al. |
| 5,571,639 A | 11/1996 | Hubbell et al. |
| 5,595,707 A | 1/1997 | Copeland et al. |
| 5,599,695 A | 2/1997 | Pease et al. |
| 5,624,711 A | 4/1997 | Sundberg et al. |
| 5,631,734 A | 5/1997 | Stern et al. |
| 5,654,199 A | 8/1997 | Copeland et al. |
| 5,677,195 A | 10/1997 | Winkler et al. |
| 5,681,755 A | 10/1997 | Noppe et al. |
| 5,737,499 A | 4/1998 | Bernstein et al. |
| 5,744,101 A | 4/1998 | Fodor et al. |
| 5,981,185 A | 11/1999 | Matson et al. |
| 6,083,726 A | 7/2000 | Mills, Jr. et al. |
| 6,093,574 A | 7/2000 | Druyor-Sanchez et al. |
| 6,670,113 B2 | 12/2003 | Hainfeld |
| 2002/0142411 A1 | 10/2002 | Hainfeld |

FOREIGN PATENT DOCUMENTS

| WO | WO 90/15070 | 12/1990 |
| WO | WO 92/10092 | 6/1992 |
| WO | WO 93/09668 | 5/1993 |
| WO | WO 97/10365 | 3/1997 |
| WO | WO03/035900 A1 | 5/2003 |

OTHER PUBLICATIONS

Merchenthaler, et al, Journal of Histochem Cytochem, vol. 37 (No. 10) p. 1563-1565 (Oct. 1989).
Meur, et al, A New Technique for Localization of Cellulase In-Situ Using Silver Nitrate, Stain Technology, vol. 58 (No. 2), (1983)Abst. only.
Partanen, A Direct Coloring Metal Precipitation Method for the Demonstration of Aryl Sulfatase A and Aryl Sulfatase B, Histochemical Journal, vol. 16 (No. 5), (1984), Abstract only.
Patton, Detection Technologies in Proteme Analysis, Journal of Chromatography B., vol. 771 (No. 1-2), p. 3-31, (May 5, 2002).
Chee, M., et al, "Accessing Genetic Information with High-Density DNA Arrays," Science, 1996, vol. 274, p. 601-614.
Danscher, G., et al, "Gold and Silver Staining: Techniques in Molecular Morphology," Apr. 2002, p. 13-69, CRS Press, Baca Raton, FL.
Meur, S.A., et al, "A New Technique for Localization of Cellulase in Situ Using Sliver Nitrate," Stain Technol., 1983, vol. 58, p. 97-100.
Partanen, S. "A Direct-Colouring, Metal Precipitation Method for the Demonstration of Arylsulphatases A and B," Histochem. J. 1984, vol. 16, p. 501-506.

(Continued)

Primary Examiner—Ann Y Lam
Assistant Examiner—James L Grun

(57) ABSTRACT

The invention is directed to novel compositions of matter and methods of detecting in situ an immunohistochemical epitope or nucleic acid sequence of interest in a biological sample comprising binding an enzyme-labeled conjugate molecule to the epitope or sequence of interest in the presence of a redox-inactive reductive species and a soluble metal ion, thereby facilitating the reduction of the metal ion to a metal atom at or about the point where the enzyme is anchored. Novel phosphate derivatives of reducing agents are described that when exposed to a phosphatase are activated to their reducing form, thereby reducing metal ions to insoluble metal.

41 Claims, 7 Drawing Sheets

OTHER PUBLICATIONS

Sia, S.K., et al, "An Integrated Approach to a Portable and Low-Cost Immunoassay for Resource-Poor Settings," Angew. Chem., Int., Ed. 43, Jan. 2004, p. 498-502.

Sigma Technical Bulletin No. 1, SE 1, Jan. 1989, Silver Enhancer Kit, Product No. SE-100, p. 1-6.

Azoulay, M., et al, "Prodrugs of anthracycline antibiotics suited for tumor-specific activation," Anticancer Drug Des. Sep. 1995, vol. 10, No. 6, p. 441-450 (Abstract only).

Bagshawe, K., et al, "Antibody-directed enzyme prodrug therapy (ADEPT) for cancer," Expert Opin. Biol. Ther., 2004, vol. 4, No. 11, p. 1777-1789.

Bakina, E., et al, "Intensely cytotoxic anthracycline prodrugs: galactosides,", Anticancer Drug Des., Dec. 1999, vol. 14, No. 6, p. 507-515 (Abstract only).

Bieniarz, C., et al, "Chromogenic Redox Assay for Beta-Lactamases Yielding Water-Insoluble Products," Analytical Biochem., 1992, vol. 207, p. 329-334.

Cheng, H., et al, "Synthesis and enzyme-specific activation of carbohydrate-geldanamycin conjugates with potent anticancer activity," J. Med. Chem., Jan. 27, 2005, vol. 48, No. 2, p. 645-652 (Abstract only).

Farquhar, D., et al, "Suicide gene therapy using *E. coli* beta-galactosidase," Cancer Chemother. Pharmacol, Jul. 2002, vol. 50, No. 1, p. 65-70 (Abstract only).

Fujimoto, Z., et al, "Crystal Structure of Rice a-Galactosidase Complexed with D-Galactose," Journal of Biological Chemistry, May 30, 2003, vol. 278, No. 22, p. 20313-20318.

Harding. F., et al, "A beta-lactamase with reduced immunogenicity for the targeted delivery of chemotherapeutics using antibody-directed enzyme prodrug therapy," Mol. Cancer Ther., Nov. 2005, vol. 4, No. 11, p. 1791-1800.

Han, H., "Targeted Prodrug Design to Optimize Drug Delivery," AAPS Pharmsci 2000, Mar. 21, 2000, vol. 2, No. 1, Article 6 (http://www.pharmsci.org/), p. 1-11.

Hult, K., et al "Enzyme promiscuity: mechanism and applications," Trends in Biotechnology, 2007, vol. 25, No. 5, p. 231-238.

Isorna, P., et al, "Crystal Structures of Paenibacillus polymyxa beta-Glucosidase B Complexes Reveal the Molecular Basis of Substrate Specificity and Give New Insights into the Catalytic Machinery of Family 1 Glycosidases," J. Mol. Biol, Aug. 31, 2007, vol. 371, No. 5, p. 1204-1218 (Abstract only).

Niculescu-Duvaz, I., et al, "Antibody-directed enzyme prodrug therapy (ADEPT): a review," Advanced Drug Delivery Reviews, 1997, vol. 26, p. 151-172.

Rooseboom, M., et al, "Enzyme-Catalyzed Activation of Anticancer Prodrugs," Pharmacol. Rev., 2004, vol. 56, p. 53-102.

Sanz-Aparicio, J., et al, "Crystal structure of beta-glucosidase A from Bacillus polymyxa: insights into the catalytic activity in family 1 glycosyl hydrolases," J. Mol. Biol. Jan. 23, 1998, vol. 275, No. 3, p. 491-502 (Abstract only).

Senter, P., et al, "Selective activation of anticancer prodrugs by monoclonal antibody-enzyme conjugates," Advanced Drug Delivery Reviews, 2001, vol. 53, p. 247-264.

Smyth, TP, et al, "Extending the beta-Lactamase-Dependent Prodrug Armory: S-Aminosulfeniminocephalosporins as Dual-Release Prodrugs," J. Org.Chem., Apr. 30, 1999, vol. 64, No. 9, p. 3132-3138 (Abstract only).

Xu, G., et al, "Strategies for Enzyme/Prodrug Cancer Therapy," Clinical Research Center, Nov. 2001, vol. 7, p. 3314-3324.

Beiniarz, C. et al, "Chromogenic Redox Assay for Beta-Lactamases Yielding Water-Insoluble Products," Analytical Biochemistry, 1992, vol. 207, p. 321-328.

Ascorbic acid-2-phosphate (AAP)

Sesamol phosphate (SP)

Hydroquinone-1,4-diphosphate (HQP)

2,2,5,7,8-Pentamethyl-6-chromanol phosphate (PMCP)

AAP    SP    SQP    PMCP

ENZYME-CATALYZED METAL DEPOSITION FOR THE ENHANCED IN SITU DETECTION OF IMMUNOHISTOCHEMICAL EPITOPES AND NUCLEIC ACID SEQUENCES

CROSS REFERENCE TO RELATED APPLICATIONS

This application claims priority to U.S. provisional application 60/482,596 filed Jun. 24, 2003, the contents of which are incorporated herein in their entirety.

BACKGROUND

1. Field of the Invention

This invention relates generally to the field of chemistry, and in particular is directed to a new method of detecting in situ immunohistochemical epitopes and nucleic acid sequences using an enzyme-mediated reaction for the localized deposition of metal atoms.

2. Description of Related Art

Tissue staining is an ancient art by modern standards that goes back over one hundred years. Recently, efforts have been made to automate the procedure of applying different types of chemical and biochemical stains to tissue sections. Instruments that have been invented for this purpose include the Ventana Medical Instruments' line of dual carousel-based instruments such as the 320, ES®, NexES®, BENCHMARK®, and the BENCHMARK® XT. Patents that describe these systems include U.S. Pat. Nos. 5,595,707, 5,654,199, 6,093,574, and 6,296,809, all of which are incorporated herein by reference in their entirety. Another type of automated stainer is the TechMate® line of stainers, described in U.S. Pat. Nos. 5,355,439 and 5,737,499, both of which are incorporated herein by reference in their entireties.

Various manual detection chemistries have been developed for histochemistry over the years. Generally, once a molecular marker or target of interest has been identified through biomolecular studies it needs to be rendered visible under the light microscope for a Pathologist or other medical specialist to interpret. The first detection step involves an anti-target primary antibody detectably labeled with biotin, digoxigenin, fluoroscein or other hapten being used to locate the biological target of interest. Next, an anti-hapten secondary antibody conjugated to an enzyme or other reporter molecule is used to locate the primary antibody. Typical enzyme systems are known to those of ordinary skill and include horseradish peroxidase or alkaline phosphatase. These enzymes then catalyze the precipitation of a chromogenic substrate in the immediate vicinity of the primary-secondary antibody complex. Chromogens such as nitro blue tetrazolium (NBT/BCIP); 3,3'-diaminobenzidene tetrahydrochloride (DAB); and 3-amino-9-ethylcarbazole (AEC) are well-known. Alternately, enzyme substate interactions may produce chemiluminesent signals, which can be captured on a photographic film.

Other labels include: $^{125}$I-labeling of the secondary antibody, which can be detected using a photographic film; fluorescein isothiocyanate-labeled second antibody, which can be detected using UV light; $^{125}$I-labeled Protein A, which can be used instead of a secondary antibody, as it will bind to the Fc region of IgG molecules; Gold-labeled secondary antibody, which is directly visible as a red color when they are bound with the secondary antibody to the primary antibody; Biotinylated secondary antibody, which when incubated with the secondary antibody, then incubated with enzyme-conjugated avidin which binds strongly to the biotin, will give an enhanced signal, as multiple biotin molecules can be attached to a single antibody molecule. Enzymes typically used include alkaline phosphatase ("AP") or horseradish peroxidase ("HRP").

Metallic enhancement of immunohistochemical detection is taught in U.S. Pat. No. 5,116,734 (Higgs et al.), incorporated herein by reference in its entirety. The '734 patent is directed to a composition of matter and a process for detecting the presence of an oxidative catalyst in a biological sample. The composition comprises a precipitate formed by oxidation of a chromogenic substrate in the presence of the catalyst, together with two or more co-precipitated reduced metals. A strong signal is formed with which to detect an oxidation catalyst which is localized to a target molecule. Target molecules may be nucleic acids, antibodies or cell surface antigens. In particular, Higgs et al. rely on a chromogenic precipitate and two or more metals, for the purpose of detecting an oxidative catalyst. Merchanthaler et al., J. Histoch. And Cytochem., 37:10 1563-65 (1989) teach silver intensification of the oxidatively polymerized DAB by pre-treating the DAB with nickel ions.

A more recent example of metallic enhancement of immunohistochemical detection includes U.S. Pat. No. 6,670,113 (Hainfeld). The '113 patent is directed to a method of producing metal in a zero oxidation state from metal ions, comprising: providing metal ions of at least one metal selected from cesium, periodic table group 1b, 2a, 4a and 8, an oxygen containing oxidizing agent and a reducing agent selected from at least one of hydroquinone, a hydroquinone derivative or n-propyl gallate; providing an oxido-reductase enzyme; combining the enzyme with the metal ions, oxidizing agent and reducing agent; and reducing at least some of the metal ions to metal in a zero oxidation state. In particular, silver ion reduction to silver metal in proximity to horseradish peroxidase when exposed to hydrogen peroxide and hydroquinone is taught.

There continues to be a need for better biochemical techniques for visually identifying immunohistochemical epitopes and DNA targets of interest via bright field light microscopy.

SUMMARY OF THE INVENTION

The invention is directed to novel compositions of matter and methods of detecting in situ an immunohistochemical epitope or nucleic acid sequence of interest in a biological sample comprising binding an enzyme-labeled conjugate molecule to the epitope or sequence of interest in the presence of a redox-inactive reductive species and a soluble metal ion, thereby catalyzing the reduction of the metal ion to a metal in oxidation state 0 at or about the point where the enzyme is anchored. Novel phosphate derivatives of reducing agents are described that when exposed to a phosphatase enzyme are activated to their reducing form, thereby reducing metal ions to insoluble metal particles in oxidation state 0.

The invention is also directed to a compound having the general structure (IV) shown below:

IV

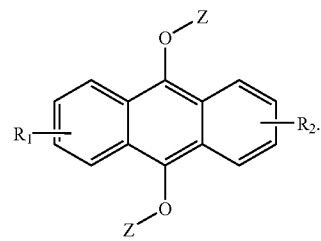

wherein $R_1$ may be H, alkyl, aryl, carboxyl, carboxyalkyl, $NH_2$, $(CH_2)_n$—COOH—, nitro, ether, thioether and sulphonate;

$R_2$ may be H, alkyl, aryl, carboxyl, carboxyalkyl, NH2, or $(CH_2)_n$—COOH—, nitro, ether, thioether and sulphonate; and Z may be $PO_3^{2-}$, H, α-galactose, β-galactose, α-glucose, β-glucose, ester, and β-lactam; but both Zs may not be H. A preferred compound has both Zs=phosphate.

The invention is also directed to a compound having the general structure (V):

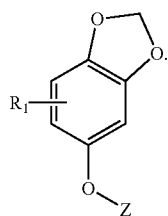

V wherein $R_1$ may be H, alkyl, aryl, carboxyl, carboxyalkyl, NH2, $(CH_2)_n$—COOH—, nitro, ether, thioether and sulphonate; and Z may be $PO_3^{2-}$, α-galactose, β-galactose, α-glucose, β-glucose, ester, and β-lactam. A particularly preferred compound has Z =phosphate.

The invention is also directed to a compound having the general structure (VI):

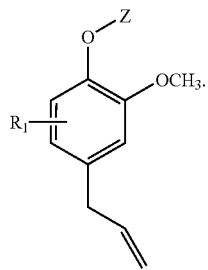

VI wherein $R_1$ may be H, alkyl, aryl, carboxyl, carboxyalkyl, NH2, $(CH_2)_n$—COOH—, nitro, ether, thioether or sulphonate; and Z may be $PO_3^{2-}$, α-galactose, β-galactose, α-glucose, β-glucose, ester, and β-lactam. A particularly preferred compound has Z=phosphate.

The invention is also directed to a compound having the general formula (VII):

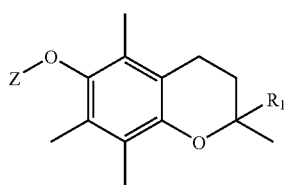

wherein $R_1$ may be H, alkyl, aryl, carboxyl, carboxyalkyl, NH2, $(CH_2)_n$—COOH—, nitro, ether, thioether and sulphonate; and Z may be $PO_3^{2-}$, α-galactose, β-galactose, α-glucose, β-glucose, ester, and β-lactam.

Two particularly preferred compounds have $R_1$=methyl or $CH_2$—$(CH_2$—$CH_2$—$CH(CH_3)$—$CH_2)_3$—H, and Z=phosphate.

The invention is also directed to a method of in situ staining a biological sample having an epitope or nucleotide sequence of interest, comprising the steps of: (a) contacting said tissue with a conjugate molecule having a hapten; (b) contacting said hapten with a hapten-binding partner conjugated to a label, enzyme; and (c) contacting said biological sample with a redox-inactive reductive species that is a substrate for said label enzyme in the presence of a metal ion.

The invention is also directed to a method of in situ staining a biological sample having an epitope or nucleotide sequence of interest, comprising the steps of: (a) contacting said tissue with a biotinylated primary antibody; (b) contacting said biological sample having said biotinylated primary antibody bound to it with streptavidin-alkaline phosphatase; and (c) contacting said biological sample of step (b) with ascorbic acid phosphate in the presence of silver ion at a pH greater than 7. An optional gold ion pretreatment step may also be applied to enhance the silver deposition.

DESCRIPTION OF THE PREFERRED EMBODIMENTS

Figure 1:
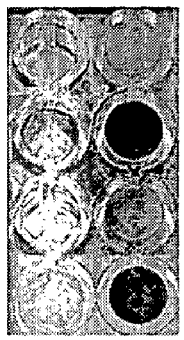
FIG. 1 is a photograph of eight microtiter wells arranged in two columns of four. Column A is the control column containing 100 μL of 50 mM silver nitrate and 100 μL of 50 mM phosphate substrate in 100 mM tris, pH 9.0. Column B contains the same components with the addition of 5 μL of 0.2 mg/mL calf-intestinal alkaline phosphatase (Pierce) in 100 mM Tris, pH 7.0. Column B demonstrates the action of alkaline phosphatase-mediated release of the reducing substrate (i.e. ascorbic acid-2-phosphate to ascorbic acid) and the concomitant reduction of silver nitrate to silver metal particles by the released reducing substrate.

The invention is directed to a method of detecting an immunohistochemical epitope or nucleic acid sequence of interest by first binding a conjugate molecule to the epitope or sequence of interest. The conjugate molecule is labeled with an enzyme which catalyzes the transfomation of a redox-inactive reductive species into a reducing agent thereby allowing the reduction of a chromogenically detectable metal at or about the point where the enzyme is anchored. More specifically, it relies on a novel method of using alkaline phosphatase and other enzymes, i.e., glucosidases, esterases, β-galactosidases as labels capable of catalyzing the dephosphorylation of a redox-inactive enzyme substrate(s), i.e. ascorbic acid phosphate, which after enzyme-catalyzed dephosphorylation becomes an extremely efficient reducing agent capable of reducing silver and/or gold ions to metallic silver and/or gold atoms. Since the reduction occurs near or at the epitope or nucleotide sequence of interest, the precipitated metallic silver/gold in oxidation state 0 accumulates in the vicinity of the epitope or sequence greatly enhancing the visual detectability of the epitope in the microscopic diagnostic procedures.

The invention is also directed to novel compounds that have been specifically synthesized for use in the above method. Most prefered is the ascorbic acid phosphate (see general formula I wherein Z is $PO_3^{-2}$ substrate, which when dephosphorylated by its enzyme alkaline phosphatase, results in ascorbate ion, a good reducer of silver and gold cations. Generally, compounds having the formulas (I)-(VII) shown below are excellent substrates.

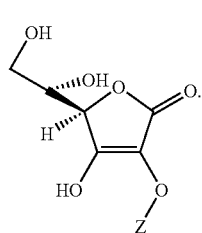

I

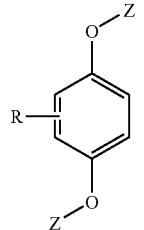

II

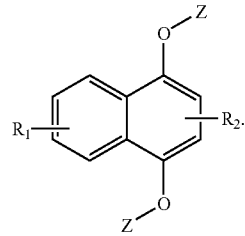

III

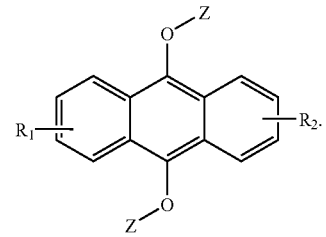

IV

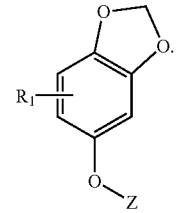

V

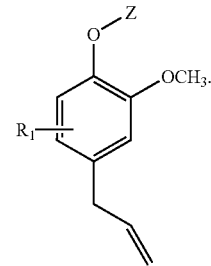

VI

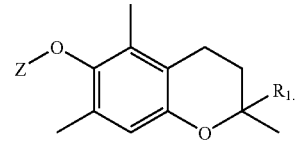

VII

For general structures I-VII, Z may be $PO_3^{2-}$, galactosyl, glucosyl, ester or beta-lactam. For general structures II-IV, one of the two Zs may also be H.

For general structures II-IV, at least one Z must be $PO_3^{2-}$, galactosyl, glucosyl, ester or beta-lactam.

For general structure II, R may be H, alky, aryl, carboxyl, carboxyalkyl, $NH_2$, $(CH_2)_n$—COOH—, nitro, ether, thioether or sulphonate.

For general structures III-VII, $R_1$ may be H, alkyl, aryl, carboxyl, carboxyalkyl, NH2, $(CH_2)_n$—COOH—, nitro, ether, thioether or sulphonate.

For general structures III-IV, $R_2$ may be H, alkyl, aryl, carboxyl, carboxyalkyl, $NH_2$, $(CH_2)_n$—COOH—, nitro, ether, thioether or sulphonate.

The terms used herein are known to the chemist of ordinary skill in the art. Nevertheless, to provide a clear and consistent understanding of the specification and claims and the scope given to such terms, the following definitions are provided:

Detecting in situ means to be able to visualize the biological feature of interest in tissue or intact cellular specimens. Tissue is for example, fixed, paraffin-embedded 4 -8 μm-thick tissue sections such as are commonly mounted on glass microscope slides and then prepared and stained for Immunohistochemistry, or in situ hybridization using oligonucleotide probes. Intact cells include cytospins, ThinPreps™ (Cytyc, Inc., Boxborough, Mass.) and other methods of preparing intact cells for staining. In situ can also refer to tissue arrays mounted on glass microscope slides.

Chromogen: Enzyme substrate that yields a detectable reaction product that is usually colored. Examples of typical chromogens include Nuclear Fast Red; nitro blue tetrazolium (NBT/BCIP); 3,3'-diaminobenzidene tetrahydrochloride (DAB); and 3-amino-9-ethylcarbazole (AEC). Many more are known and available through suppliers such as Pierce Chemical, Rockford, Ill.

Conjugate molecule: may be any molecule that has a complementary binding portion that, when brought into proximity to its complementary binding site, binds to the site. Antibodies and RNA/DNA oligomers that have sequences capable of hybridizing to their target RNA or DNA, are two examples of conjugate molecules. Yet another conjugate pair is the streptavidin-biotin pair, also called "affinity partners" herein. The conjugate protein streptavidin has a natural affinity for biotin. Biotin is used pervasively throughout the anatomical pathology laboratory as streptavidin's binding partner. Almost all commercially-available primary antibodies are labeled with biotin so that streptavidin conjugates can be used to localize the primary antibody. In the present invention the biotin-streptavidin binding motif is used to co-localize streptavidin with AP. Secondary antibodies labeled with biotin are targeted to the binding site in the tissue, and the streptavidin-AP conjugate brings the AP into the same location through streptavidin's binding to biotin.

Kit: a packaged combination of one or more vessels, containers, devices or the like holding the necessary reagents for detecting a biomarker of interest. The kit is appended with written instructions for performing the method. The kit may contain an AP-labeled antibody, nucleic acid, ligand, or the like. The kit for detecting a biomarker of interest in a biological sample comprises one or more containers, each container adapted to hold an anti-biomarker conjugate molecule, a redox-inactive reductive species, an enzyme for rendering said reductive species active, and a metal ion.

The label enzyme may be alkaline phosphatase or other enzyme conjugated to an antibody, nucleic acid or conjugate protein such as streptavidin. The function of the label enzyme is to catalyze the creation of a redox-active reductive species from a redox-inactive reductive precursor. Other enzymes may be alpha- and beta-galactosidases, alpha- and beta-glucosidases, esterases generally, and beta-lactamases, specifically cephalosporinases and penicillinases.

The redox-inactive reductive species is the precursor to the reductive species/reducing agent such as ascorbate or hydroquinone dianion, which under the proper conditions will reduce soluble metal ions such as silver(+) or gold (+3) to a silver or gold atom such that it becomes visible under a brightfield light microscope to the eye as a specific dot. A preferred redox-inactive reductive species of the pfesent invention is ascorbate phosphate, although many more are taught herein.

Other reducing agents that can be used to amplify the silver signal are hydroquinone, ascorbic acid, 2-aminophenol and 4-aminophenol. They act to further reduce metal ions to metallic oxidation state 0, and are typically used to supplement or amplify the signal. Other reducing agents are well-known to those of ordinary skill in the art, and can be substituted for those taught herein.

The invention disclosed herein utilizes a novel series of phosphates and diphosphates and related derivatives which, although completely inactive as reducing agents, become reactive and capable of reducing metal ions to metallic oxidation state (0) after the alkaline phosphatase-catalyzed hydrolysis of the phosphate groups. The inactive precursor reducing agent shown in the structures below is ascorbic acid phosphate, a particularly preferred embodiment. In the presence of alkaline phosphatase it is hydrolyzed to the active reducing agent ascorbic acid, which is capable of reducing gold, silver and other metal cations to metal(0):

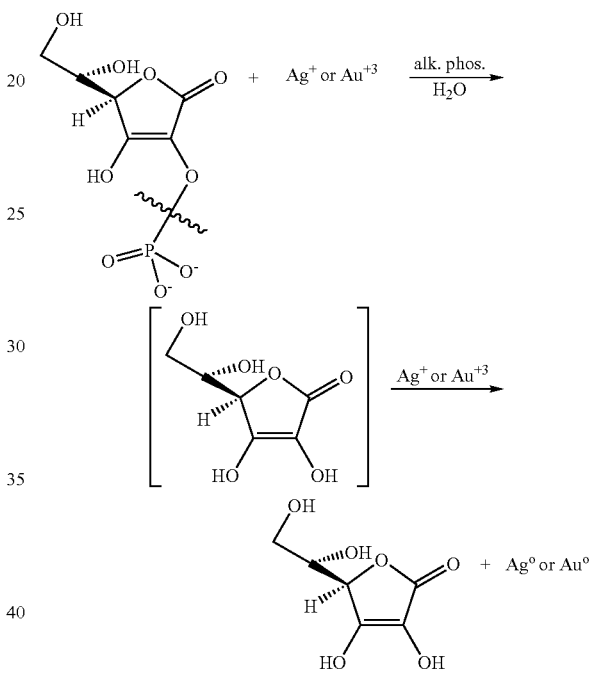

Still other novel organic reducing agent precursors include α-tocopherol phosphate, sesamol phosphate and eugenol phosphate, shown in the general structures V-VII, wherein $Z=PO_3^{-2}$; and R may be H, alkyl, aryl, carboxyl, carboxyalkyl, $NH_2$, $(CH_2)_n$—COOH—, nitro, ether, thioether or sulphonate.

There are several advantages of using alkaline phosphatase as a label and ascorbate phosphate as the substrate in the instant invention:

(1) Alkaline phosphatase is one of the perfectly evolved enzymes with a Kcat/Km approximating the diffusion-controlled limit of $1\times10^9$ liter/mole-sec.

(2) Alkaline phosphatase's optimal pH is 9-10, coinciding with the fastest reduction potentials of the hydroquinones liberated by the dephosphorylation of the substrates.

(3) Aryl and alkyl phosphates and diphosphates can be synthesized reasonably inexpensively.

(4) Aryl and alkyl phosphates and diphosphates are excellent substrates of alkaline phosphatase.

(5) Aryl and alkyl phosphates and diphosphates are generally reasonably stable and can be formulated to resist decomposition over extended periods.

(6) Alkaline phosphatases are very stable enzymes resisting thermal and chemical degradation better than most enzymes.
(7) Alkaline phosphatases are reasonably small and methods of conjugation to other biological molecules have been developed.
(8) Ascorbic acid phosphate is an excellent substrate of AP and ascorbate has a very high reduction potential, i.e., it reduces $Ag+$ and $Au+3$ quantitatively and rapidly, with dehydroascorbate as the only by-product.

Another excellent reducing agent is hydroquinone dianion. The structures below show the hydroquinone-benzoquinone equilibrium structures, at a pH of from 9-10, in the presence of an electron acceptor like silver cation. Hydroquinone dianion is the actual species responsible for reducing silver cations to insoluble metal. The formation of benzoquinone is favored at high pH:

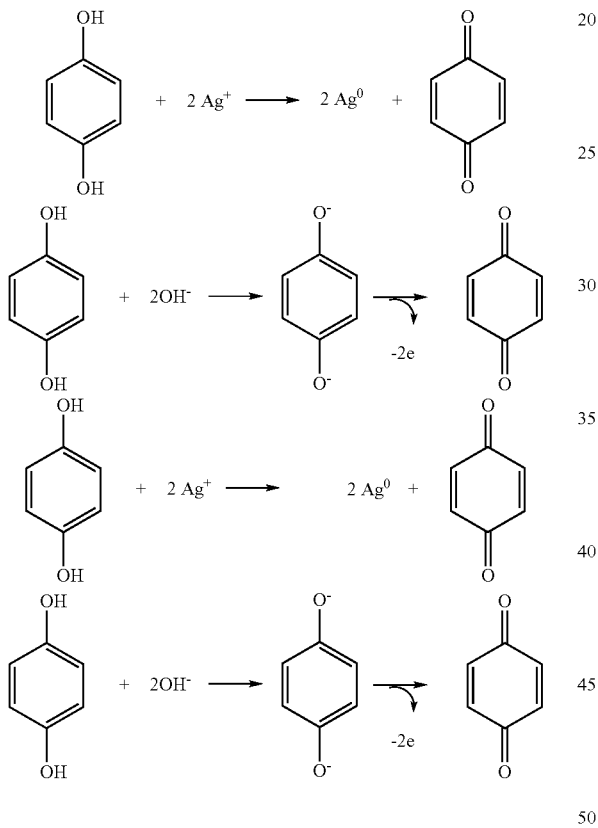

General structures II-IV are some hydroquinone derivatives that are also the subject of this invention. Hydroquinone diphosphate (general structure II with both Zs=phosphate) is a preferred substrate for dephosphorylation by the enzyme alkaline phosphatase, which at pH 7-11 is dephosphorylated to hydroquinone dianion, a preferred reducing agent for silver cation. Other hydroquinone-like derivatives are depicted in general structures III-IV, and are naphthohydroquinone (III), and anthrahydroquinone (IV). They can be substituted as shown within the aryl rings at any position with $R_1$ and $R_2$, and at the oxygens with Z. Substituents $R_1$ and $R_2$ can be just about any moiety that can be reacted at these sites, yet still retain the ability to generate a dianion at the desired pH. An exhaustive list of organic substituents is not included herein, but some likely substituents include the following: H, alkyl, aryl, carboxyl, carboxyalkyl, $NH_2$, $(CH_2)_n$—COOH—, nitro, ether, thioether and sulphonate.

Various enzyme labels may be used in the instant invention, depending upon the label-substrate pair selected, as shown in the structures below. For example, esterases may be used in conjunction with mono- and diesters. Galactosidases and glucosidases may also be employed for deprotection of the substrates mono- and di-galactosides and mono- and diglucosides. The "Z" groups which are shown below include phosphate, galactosyl, glucosyl, esters, and beta-lactams. A preferred beta-lactam is cephalosporine. The saccharides that come within the scope of the invention include any with reducing end conjugated to the reductive species' oxygen. R groups may be H, alkyl, aryl, carboxyl, carboxyalkyl, $NH_2$, $(CH_2)_n$—COOH—, nitro, ether, thioether or sulphonate.

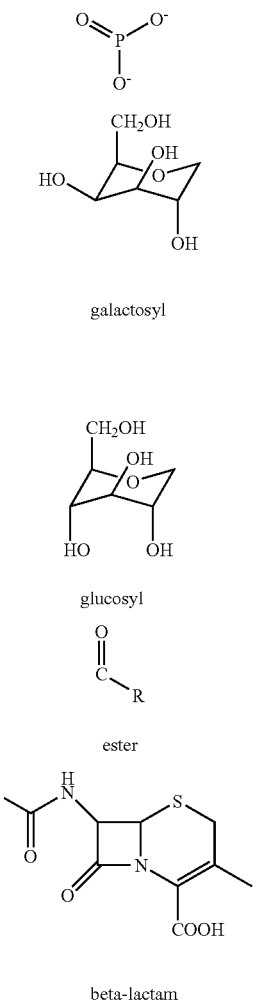

The last structure, a C3' beta-lactams (i.e. cephalosporins) may also be used in conjunction with the beta-lactamases as enzymatic labels'. The R group of the beta-lactams may be an alkyl aryl, i.e., thiophene, methyl or benzyl.

Of particular value and interest are the galactosyl, glucosyl and other saccharide hydroquinone and ascorbate derivatives in that the enzyme turnover of the inactive substrate yields TWO reducing agents, namely hydroquinone or ascorbate and the carbohydrate with its reducing end also capable of reducing the silver ion to metallic silver:

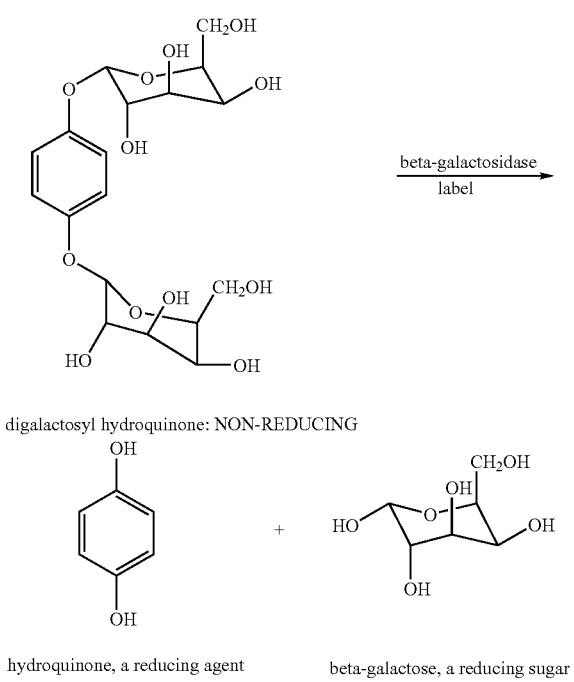

digalactosyl hydroquinone: NON-REDUCING hydroquinone, a reducing agent + beta-galactose, a reducing sugar In addition to alkaline phosphatase, acid phosphatase may also be used as a label in which case the deprotection of the phosphate groups on the substrates should be done at pH<7. Ascorbic acid liberated in such reactions still conserves excellent reducing capabilities at pH<7.

A gold pretreatment step may be utilized to "seed" the area immediately adjacent to the immobilized alkaline phosphatase, thereby taking advantage of the well-known propensity for silver metal to deposit on a nucleation site such as gold particles ("metallography"). As demonstrated in the Examples herein, once the SA-AP conjugate was bound to the biotinylated conjugate molecule, gold ion in the form of $AuCl_3$ together with ascorbate phosphate was co-deposited. AP dephosphorylated the ascorbate phosphate resulting in production of the reducing agent ascorbate, which then reduced gold ions to metallic gold. Metallic gold then served as the nucleation site for further amplification of the signal by silver ion reduction to silver metal.

The following examples are included for purposes of illustrating certain aspects of the invention and should not be construed as limiting.

EXAMPLES

Example 1

Phosphates for Alkaline-Phosphatase Mediated Reduction of Silver (I)

Silver nitrate (100 μL of 50 mM $AgNO_3$) was aliquoted into the wells of a microtiter plate (see FIG. 1). Addition of 100 μL of a 50 mM solution of either ascorbic acid-2-phosphate (wells A1, B1), sesamol phosphate (wells A2, B2), hydroquinone-1,4-diphosphate (wells A3, B3), or 2,2,5,7,8-pentamethyl-6-chromanol phosphate (wells A4, B4) to the silver solution did not elicit any reaction. If calf-intestinal alkaline phosphatase (5 μL of 0.2 mg/mL) was added to the Column B wells, each solution formed metallic silver (0) as either a fine, black precipitate or silvering of the container walls.

A: 100 μL of 50 mM $AgNO_3$ and 100 μL of 50 mM substrate phosphate

B: 100 μL of 50 mM $AgNO_3$, 100 μL of 50 mM substrate phosphate, and 5 μL of 0.2 mg/mL calf-intestinal alkaline phosphatase (Pierce Chemical, Rockford, Ill.) in 100 mM Tris, pH 7.0.

Example 2

Figure 2:
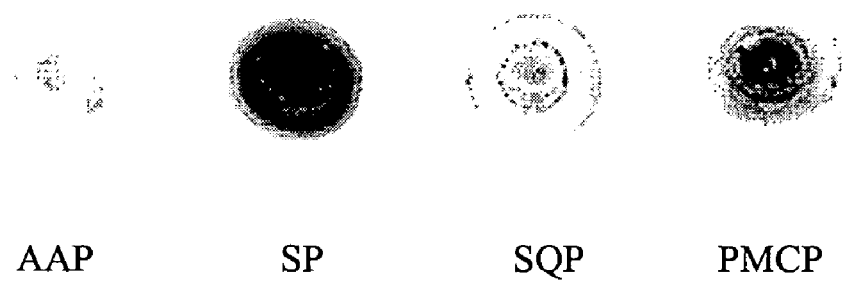
FIG. 2 is a photograph of four spots on nitrocellulose paper that were treated with 5 μL of 0.2 mg/mL calf-intestinal alkaline phosphatase (Pierce) in 100 mM Tris, pH 7.0, 5 μL of a 50 mM solution of the phosphates from Example 1 in 100 mM Tris, pH 9.0, and 5 μL of 50 mM silver nitrate. Ascorbic acid-2-phosphate (AAP), Sesamol phosphate (SP), Hydroquinone-1,4-diphosphate (HQP), 2,2,5,7,8-Pentamethyl-6-chromanol phosphate (PMCP).

Alkaline Phosphatase, Silver Nitrate, and Substrate Phosphates on Nitrocellulose Alkaline phosphatase (5 μL of 0.2 mg/mL) was added to nitrocellulose paper and dried (see FIG. 2). Each of the phosphates were spotted on the nitrocellulose as 5 μL of 0.05M solution in 0.1M Tris, pH 9. When 5 μL of 0.05M $AgNO_3$ was added to each dried spot, a black precipitate was observed only at the spot where alkaline phosphatase was applied.

Example 3

Offline Development of Ag Nanoparticles on Tonsil Using the AP-SA Conjugate at High pH The preparation of the slides for analysis was done on a Ventana Benchmark® automated staining instrument (Ventana Medical Systems, Inc., Tucson, Ariz.). The slides were removed for manual development of signal. The use of the term "buffer" within this Example refers to a 0.1 M Tris buffer (Trizma base (Sigma-Aldrich) in dI $H_2O$ pH to 9 using glacial acetic acid (Sigma-Aldrich). The following is the adapted procedure from the instrument: the paraffin-coated tissue on the slide was heated to 75° C. for 4 minutes and treated twice with EZPrep™ (Ventana, Tucson, Ariz.) volume adjusted at 75° C. before application of the liquid cover slip with EZPrep volume adjust. After 4 minutes at 75° C., the slide was rinsed and automated deparaffinization volume adjust was added along with liquid cover slip to deparaffinize the tissue at 76° C. for 4 minutes. The slide was cooled to 40° C. and rinsed three times before the addition of ANTI-CD20 antibody (clone L26, Ventana, Tucson, Ariz.) followed by liquid cover slip and incubation at 40° C. for 16 minutes. After rinsing the slide, the tissue was treated with biotinylated Universal Secondary Antibody (Ventana Medical Systems, part # 760-4205) to co-locate biotin with the Anti-CD20 antibody, followed by liquid cover slip and incubation at 40° C. for 8 minutes. The slide was rinsed twice and removed from the instrument and stored in 1X Reaction Buffer (Ventana, Tucson, Ariz.) until they were ready to be developed.

The slide was removed from 1X Reaction Buffer and rinsed 10 times with buffer followed by the addition of 300 μL of buffer to the slide as well as 100 μL of AP-SA conjugate (0.14 mg/mL in buffer, Sigma-Aldrich). The slide was incubated at 37° C. for 15 minutes followed by rinsing ten times with buffer. The slide was treated with 300 μL of the buffer followed by 50 μL of $AuCl_3$ (Sigma-Aldrich) (2.5 μg/mL in buffer) and 50 μL of ascorbic acid phosphate (Sigma-Aldrich) (0.1 M in buffer). The slide was incubated at 37° C. for 20 minutes and followed by rinsing 10 times with buffer. The slide was treated with 300 μL of buffer followed by 50 μL of silver acetate (Sigma-Aldrich) (0.1 M in buffer) and 50 μL of the ascorbic acid phosphate solution and incubated at 37° C. for 20 minutes. The slide was again rinsed 10 times with buffer followed by the application of ISH Red Counterstain (Ventana, Tucson, Ariz.) as a counter-stain. The slide was incubated with the counter-stain for 3 minutes and rinsed with buffer. Dehydration of the slide with ethanol and xylene preceded the application of the coverslip, after which the slides were viewed under the microscope.

Figure 3:
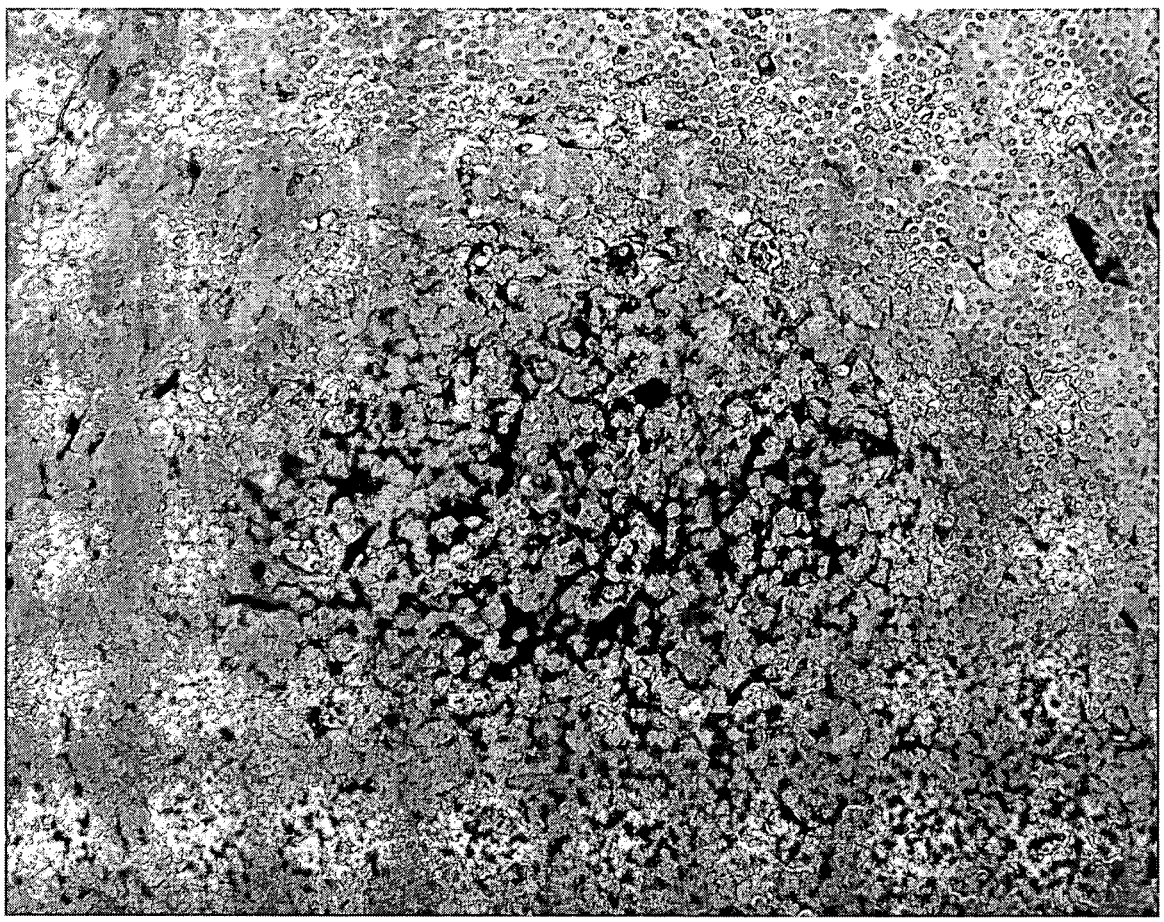
FIG. 3 is a gray-scale photomicrograph of normal tonsil tissue stained using AP-SA conjugate, gold pre-treatment, and silver reduction using ascorbic acid phosphate (AAP).
Figure 5:
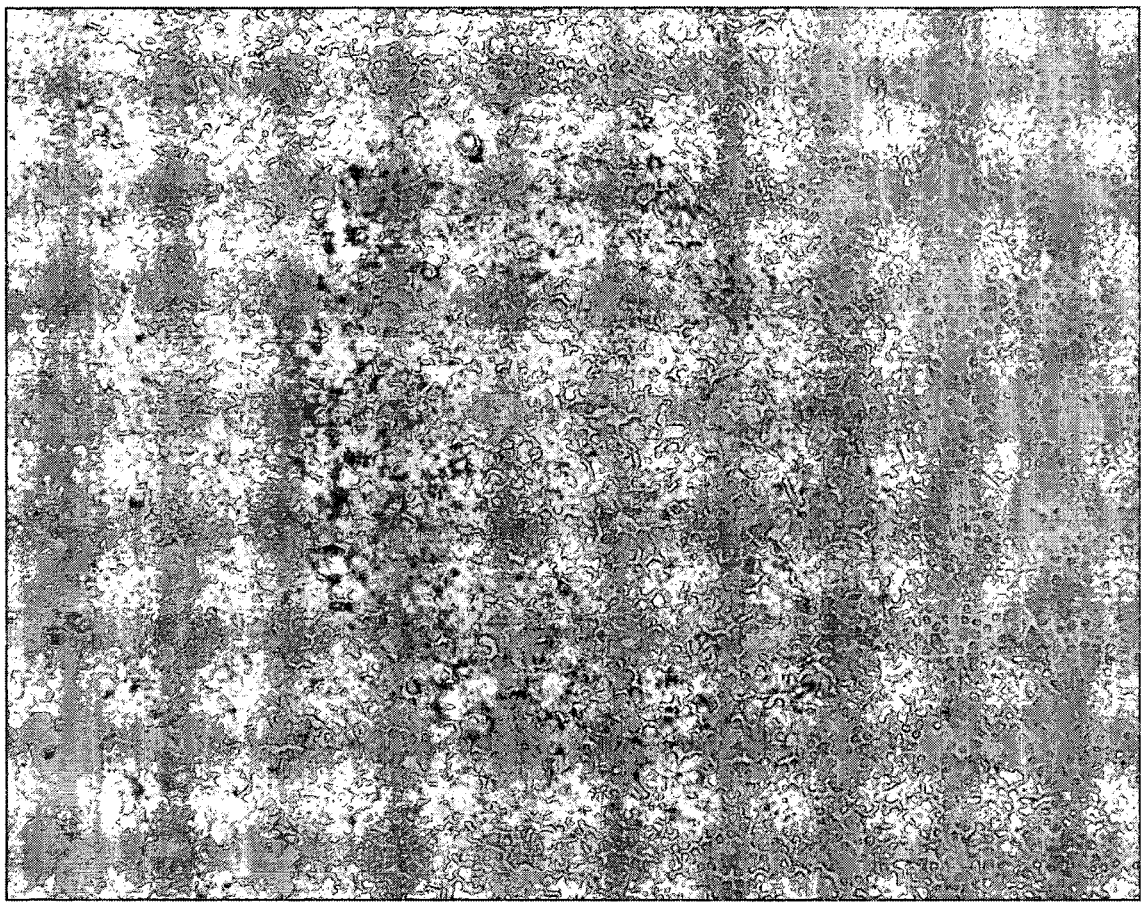
FIG. 5 is a gray-scale photomicrograph of the positive control for FIGS. 3-4.

As shown by the gray-scale photographs in FIG. 3, staining is present in the plasma membrane and cytoplasmic regions of normal B cells in normal tonsil. Staining intensity is comparable to positive control (FIG. 5) detected with Enhanced V-Red Detection kit (Ventana, Tucson, Ariz.).

Example 4

Online Development of Ag Nanoparticles on Tonsil Using the AP-SA Conjugate at High pH The main difference between this example and Example 3 is that this example shows full automation of the staining steps, while in Example 3 the slide was removed from the instrument prior to development with AP-SA. The preparation of the slides for analysis was done on a Ventana Benchmark Instrument. The use of the term "buffer" within this Example refers to a 0.1 M Tris buffer (Trizma base-Sigma-Aldrich) in deionized $H_2O$ pH to 9 using glacial acetic acid (Sigma-Aldrich). The following is the adapted procedure from the instrument: the paraffin-coated tissue on the slide was heated to 75° C. for 4 minutes and treated twice with EZPrep volume adjust at 75° C. before application of the liquid cover slip with EZPrep volume adjust. After 4 minutes at 75° C., the slide was rinsed and automated deparaffinization volume adjust was added along with liquid cover slip to deparaffin the tissue at 76° C. for 4 minutes. The slide was cooled to 40° C. and rinsed three times before the addition of ANTI-CD20 antibody (clone L26, Ventana, Tucson, Ariz.) followed by liquid cover slip and incubation at 40° C. for 16 minutes. After rinsing the slide, the tissue was treated with biotinylated Universal Secondary Antibody (Ventana Medical Systems, part # 760-4205) to co-locate biotin with the Anti-CD20 antibody, followed by liquid cover slip and incubation at 40° C. for 8 minutes. The slide was rinsed twice with buffer followed by the application of liquid cover slip and the addition of AP-SA conjugate (Sigma-Aldrich, 100 µL, 0.14 mg/mL in buffer) and incubation at 37° C. for 16 minutes. The slide was rinsed with buffer, liquid cover slip was applied and this was followed by the addition of 100 µL of a 1:1 solution of $AuCl_3$ (Sigma-Aldrich) (1.25 µg/mL) and ascorbic acid phosphate (Sigma-Aldrich) (0.05 M) in buffer. The slide was incubated at 37° C. for 20 minutes, rinsed with buffer and coated with liquid cover slip. A total of 100 µL of a 1:1 solution of silver acetate (Sigma-Aldrich) (0.05 M) and ascorbic acid phosphate (0.05 M) was added to the slide, and the slide was incubated for 20 minutes at 37° C. The slide was rinsed three times with buffer and treated to a detergent wash before dehydration with ethanol and xylene and subsequent application of a cover slip to the slide, after which the slide was viewed through a microscope.

Figure 4:
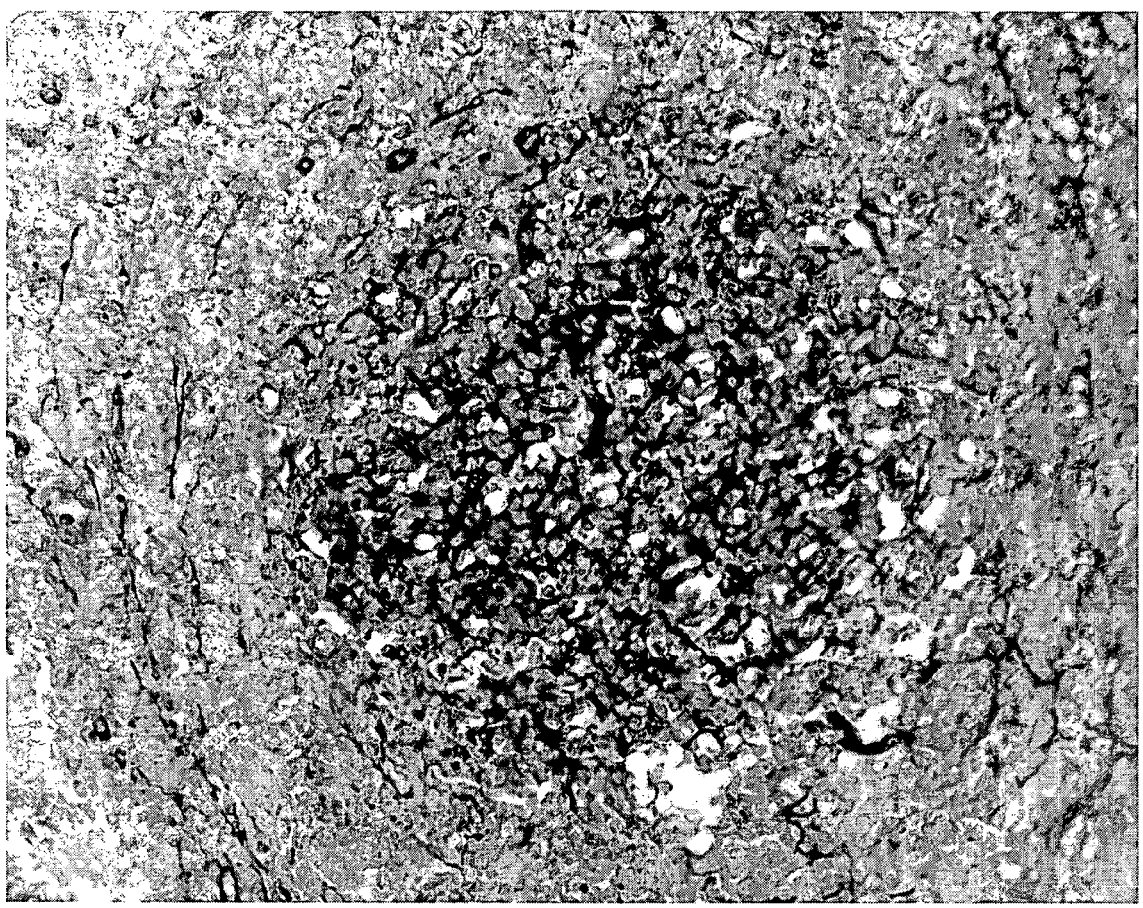
FIG. 4 is a gray-scale photomicrograph of normal tonsil tissue stained using AP-SA conjugate, gold pre-treatment, and silver reduction using AAP, the only difference being full online development of the silver signal.

As shown by the gray-scale photographs in FIG. 4, staining is present in the plasma membrane and cytoplasmic regions of normal B cells in normal tonsil. Staining intensity is comparable to positive control (FIG. 5) detected with Enhanced V-Red Detection kit (Ventana, Tucson, Ariz.).

Example 5

Anti-Desmin on Skeletal Muscle

Figure 6:
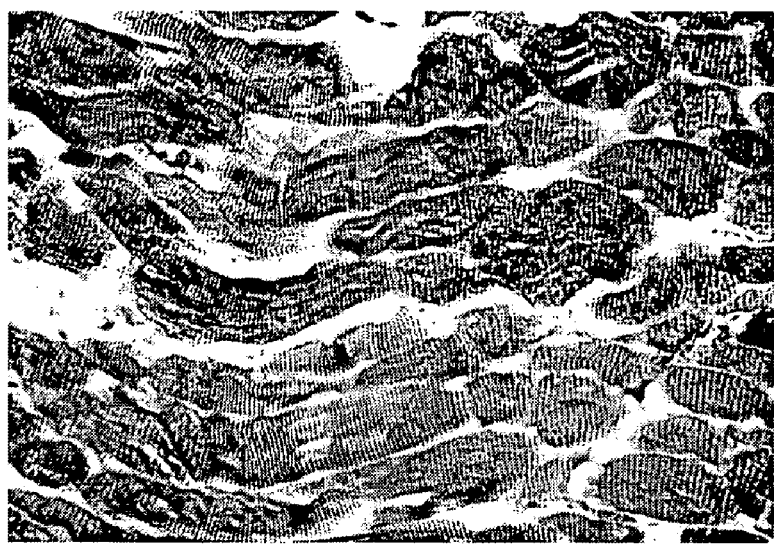
FIG. 6 is a photomicrograph of anti-Desmin antibody on skeletal muscle detected with gold pretreatment, AAP and $AgNO_3$, 20 minutes incubation.

Formalin-fixed, paraffin-embedded skeletal muscle was sectioned and placed on glass slides for light microscopy. Sections were deparaffinized on a Ventana Medical Systems' BenchMark slide stainer. Remaining on the BenchMark, the section was treated with Protease 1 (Ventana) for 4 minutes. Sections were then incubated with Anti-Desmin (Ventana, cat# 760-2513) monoclonal antibody for 16 minutes at 37° C. After washing with Reaction Buffer on the instrument, a rabbit anti-mouse antibody was incubated for 8 minutes at 37° C. Sections were then rinsed with Reaction Buffer and incubated with a mouse anti-rabbit antibody for 8 minutes at 37° C. (Amplification Kit, Ventana cat. no. 760-080). Next the sections were rinsed with Reaction Buffer and incubated with a cocktail of biotinylated secondary antibodies biotinylated Universal Secondary Antibody (Ventana Medical Systems, part # 760-4205) for 8 minutes at 37° C. The sections were rinsed and a solution of streptavidin-alkaline phosphatase (Enhanced SA-/Alk Phos/VRed Ventana, cat. no. 253-2181) was incubated for 16 minutes at 37° C. The sections were then removed from the BenchMark slide stainer. The slides were then washed with dI $H_2O$ and incubated with 500 µl of 2.5µg/ml hydrogen tetrabromoaurate (III) hydrate (Aldrich cat. no. 44,212) for 4 minutes at 37° C. The solution was rinsed with $dIH_2O$ and 250 µl of 50 mM $AgNO_3$ (Sigma #S-0139) in 0.5 M Tris Buffer at pH 9.0 and 250 µl of 100 mM ascorbic acid phosphate (Sigma A-8960) in a 0.5M DEA Buffer at pH 10.0 with 5% PVA (av. mol wt 70,000 to 100,000 Sigma # P-1763) was applied to each section. The slides were allowed to incubate for 20 minutes at 37° C. The slides were rinsed with dI $H_2O$ and coverslipped without counterstain. Results are shown in FIG. 6.

Example 6

Anti-S100 on Brain

Figure 7:
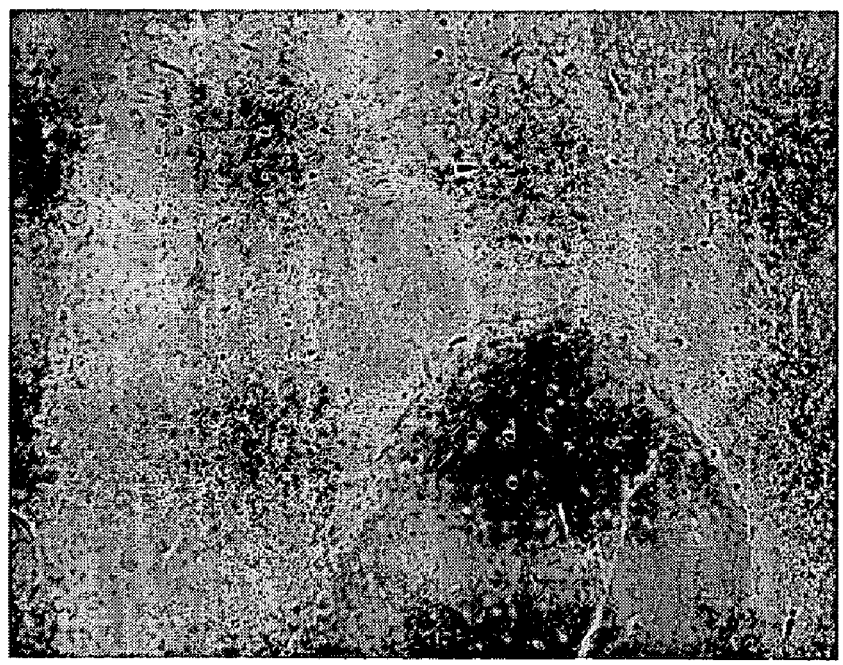
FIG. 7 is a photomicrograph of anti-S100 on brain, detected with gold pretreatment, AAP and $AgNO_3$, 20 minutes incubation.

Formalin-fixed paraffin-embedded brain tissue was sectioned and placed on glass slides for light microscopy. Sections were deparaffinized on a Ventana BenchMark slide stainer. Sections were then incubated with Anti-S100 polyclonal antibody (Ventana cat. no. 760-2523) for 16 minutes at 37° C. Next the sections were rinsed with Reaction Buffer and incubated with a cocktail of biotinylated secondary antibodies biotinylated Universal Secondary Antibody (Ventana Medical Systems, part # 760-4205) for 8 minutes at 37° C. The sections were rinsed and a solution of streptavidin-alkaline phosphatase (Enhanced SA-/Alk PhosNVRed Ventana, cat. no. 253-2181) was incubated for 16 minutes at 37° C. The sections were then removed from the BenchMark slide stainer. The slides were then washed with dI $H_2O$ and incubated with 500 µl of 2.5 µg/ml hydrogen tetrabromoaurate (III) hydrate (Aldrich #44,212) for 4 minutes at 37° C. The solution was rinsed with $dIH_2O$ and 250 µl of 50 mM $AgNO_3$ (Sigma #S-0139) in 0.5 M Tris Buffer at pH 9.0 and 250µl of 100 mM ascorbic acid phosphate in a 0.5 M (Sigma A-8960) DEA Buffer at pH 10.0 with 5% PVA (av. mol wt 70,000 to 100,000 Sigma # P-1763)) was applied to each section. The slides were allowed to incubate for 20 minutes at 37° C. The slides were counterstained with Nuclear Fast Red and coverslipped. Results are shown in FIG. 7.

Example 7

Rabbit Negative Control on Brain

Formalin-fixed paraffin-embedded skeletal muscle was sectioned and placed on glass slides for light microscopy. Sections were deparaffinized on a Ventana BenchMark slide stainer. Sections were then incubated with Rabbit Negative Control (Ventana, cat. no. 760-2023) for 16 minutes at 37° C. Next the sections were rinsed with Reaction Buffer and incubated with a cocktail of biotinylated secondary antibodies biotinylated Universal Secondary Antibody (Ventana Medical Systems, part # 760-4205) for 8 minutes at 37° C. The sections were rinsed and a solution of streptavidin-alkaline phosphatase (Enhanced SA-/Alk PhosNVRed Ventana, cat. no. 253-2181) was incubated for 16 minutes at 37° C. The sections were then removed from the BenchMark slide stainer. The slides were then washed with dI $H_2O$ and incubated with 500 µl of 2.5 µg/ml hydrogen tetrabromoaurate (III) hydrate (Aldrich #44,212) for 4 minutes at 37° C. The solution was rinsed using di$H_2O$ and 250 µl of 50 mM $AgNO_3$ (Sigma #S-0139) in 0.5 M Tris Buffer at pH 9.0 and 250 µl of 100 mM ascorbic acid phosphate (Sigma A-8960) in a 0.5 M DEA Buffer at pH 10.0 with 5% PVA (av. mol wt 70,000 to 100,000 Sigma # P-1763)) was applied to each section. The slides were allowed to incubate for 20 minutes at 37° C. The slides were counterstained with Nuclear Fast Red and coverslipped. Results are shown in FIG. 8.

Figure 8:
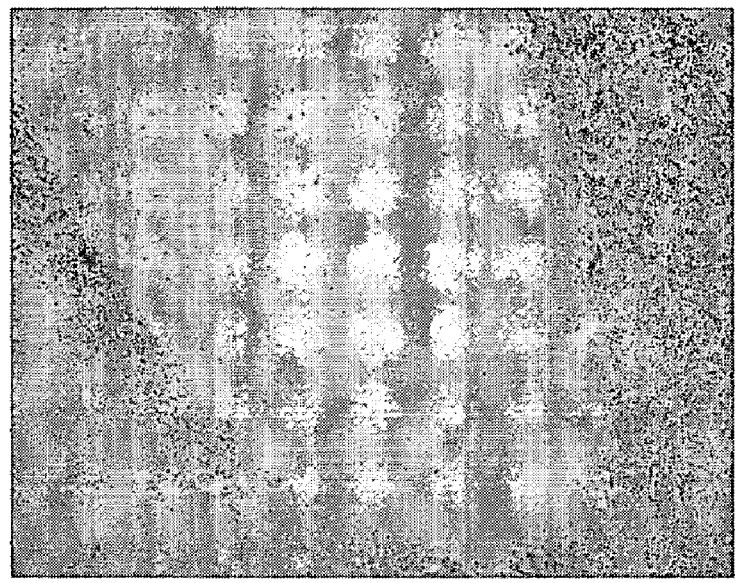
FIG. 8 is a photomicrograph of Rabbit Negative Control on Brain detected with gold pretreatment, AAP and $AgNO_3$, 20 minutes incubation.
Figure 9:
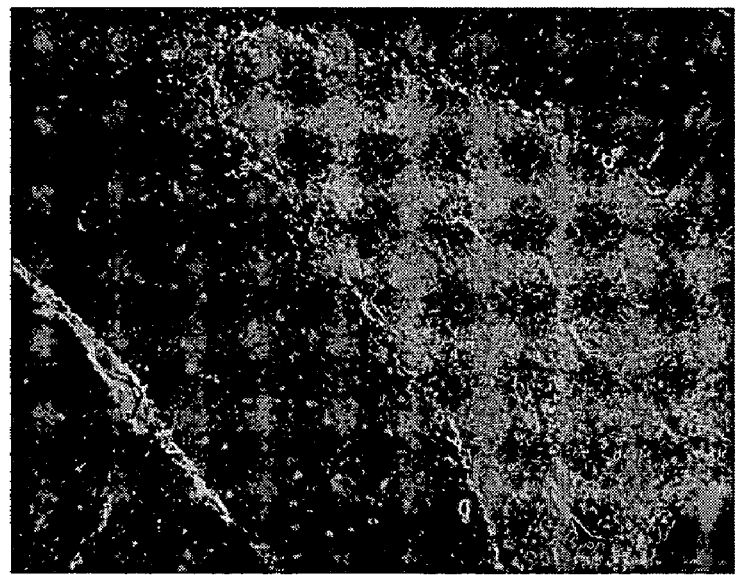
FIG. 9 is a photomicrograph of anti-S100 antibody on brain tissue, using Ventana VRed detection.

The grey-black staining observed with FIG. 7 compared to the lack of grey-black staining observed with FIG. 8 demonstrates that the staining pattern in FIG. 7 is specific for the antigen since FIG. 8 was run with Negative Rabbit Control. FIG. 9 is the same case of brain tissue run with Anti-S100 but detected utilizing Ventana's Enhanced V-Red Detection Kit. Observe that the staining pattern is the same as that found in FIG. 7.

Example 8

Anti-Desmin on Skeletal Muscle with Non-enzymatic Amplification

Figure 10:
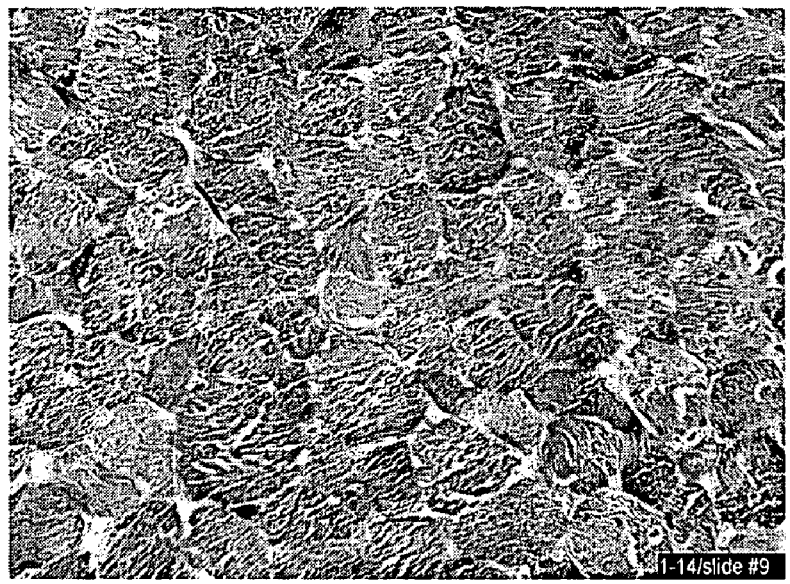
FIG. 10 is a photomicrograph of anti-Desmin antibody on Skeletal Muscle, gold pretreatment, AAP and $AgNO_3$, 10 minutes incubation, and 10 minutes' 4-methylaminophenol amplification.

This example shows that chemical amplification of the silver signal can be used to amplify the original silver deposited as a function of reduction by ascorbate. Formalin-fixed paraffin-embedded skeletal muscle was sectioned and placed on glass slides for light microscopy. Sections were deparaffinized on a Ventana BenchMark slide stainer. Remaining on the BenchMark, the section was treated with Protease 1 (Ventana) for 4 minutes. Sections were then incubated with Anti-Desmin (Ventana, cat. no. 760-2513) monoclonal antibody for 16 minutes at 37° C. After washing with Reaction Buffer on the instrument, a rabbit anti-mouse antibody was incubated for 8 minutes at 37° C. Sections were then rinsed with Reaction Buffer and incubated with a mouse anti-rabbit antibody for 8 minutes at 37° C. (Amplification Kit, Ventana cat. no. 760-080). Next the sections were rinsed with Reaction Buffer and incubated with a cocktail of biotinylated secondary antibodies biotinylated Universal Secondary Antibody (Ventana Medical Systems, part # 760-4205) for 8 minutes at 37° C. The sections were rinsed and a solution of streptavidin-alkaline phosphatase (Enhanced SA-/Alk Phos/VRed, Ventana cat. no. 253-2181) was incubated for 16 minutes at 37° C. The sections were then removed from the BenchMark slide stainer. The slides were then washed with dI $H_2O$ and incubated with 500 µl of 2.5 µg/ml hydrogen tetrabromoaurate (III) hydrate (Aldrich #44,212) for 4 minutes at 37° C. The solution was rinsed with dI$H_2O$ and 250 µl of 50 mM $AgNO_3$ (Sigma #S-0139) in 0.5 M Tris Buffer at pH 9.0 and 250 µl of 100 mM ascorbic acid phosphate (Sigma A-8960) in a 0.5M DEA Buffer at pH 10.0 with 5% PVA (av. mol wt 70,000 to 100,000 Sigma # P-1763)) was applied to each section. The slides were allowed to incubate for 10 minutes at 37° C. The slides were rinsed with dI $H_2O$. The signal was then amplified by incubating for 10 minutes at 37° C. in a 25 mM 4-Methyl aminophenol (Aldrich # 129720), 12 mM $AgNO_3$ solution in a 0.1 M Citrate Buffer at pH 3.8. FIG. 10 demonstrates the signal with the amplification when compared to Example 9 (FIG. 11) which is without any non-enzymatic amplification.

Example 9

Anti-Desmin on Skeletal Muscle without Non-enzymatic Amplification

Figure 11:
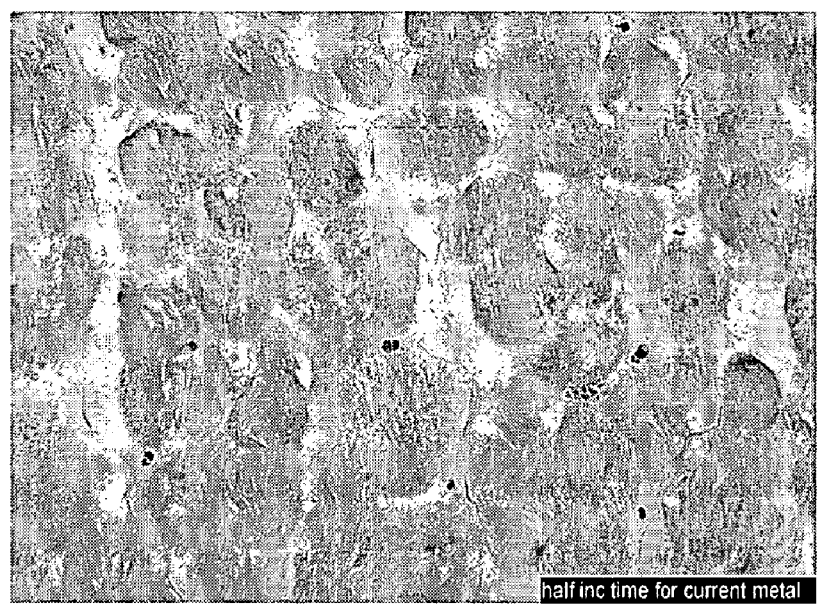
FIG. 11 is a photomicrograph of anti-Desmin antibody on Skeletal Muscle without any non-enzymatic amplification. Same conditions as in FIG. 9, except no amplification step.

Formalin-fixed paraffin-embedded skeletal muscle was sectioned and placed on glass slides for light microscopy. Sections were deparaffinized on a Ventana Medical Systems' BenchMark slide stainer. Remaining on the BenchMark, the section was treated with Protease 1 for 4 minutes. Sections were then incubated with Anti-Desmin monoclonal antibody for 16 minutes at 37° C. After washing with Reaction Buffer, on the instrument, a rabbit anti-mouse antibody was incubated for 8 minutes at 37° C. Sections were then rinsed with Reaction Buffer and incubated with a mouse anti-rabbit antibody for 8 minutes at 37° C. Next the sections were rinsed with Reaction Buffer and incubated with a cocktail of biotinylated secondary antibodies. The sections were rinsed and a solution of Strept-Avidin Alkaline Phosphatase was incubated for 16 minutes. The sections were then removed from the BenchMark Automated slide stainer. The slides were then washed with dI $H_2O$ and incubated with 500 µl of 2.5 µg/ml hydrogen tetrabromoaurate (III) hydrate for 4 minutes at 37° C. The solution was rinsed with dI$H_2O$ and 250 µl of 50 mM $AgNO_3$ in 0.5 M Tris Buffer at pH 9.0 and 250 µl of 100 mM Ascorbic Acid Phosphate in a 0.5M DEA Buffer at pH 10.0 with 5% PVA (av. mol wt 70,000 to 100,000) was applied to each section. The slides were allowed to incubate for 10 minutes at 37° C. The slides were rinsed with dI $H_2O$. FIG. 11 demonstrates the signal without the amplification when compared to Example 8 (FIG. 10).

Example 10

Synthesis of Hydroquinone-1,4-diphosphate

Hydroquinone was reacted with two equivalents of phosphorous oxychloride and two equivalents anhydrous pyridine in anhydrous toluene (to 0.1 M) over 30 minutes. The mixture was refluxed for an additional 30 minutes and allowed to cool to ambient temperature. Pyridinium chloride was removed by filtration through a pad of diatomaceous earth and rinsed with a small volume of dry toluene. The filtrate was concentrated in vacuo at 40° C. and the residue hydrolyzed with aqueous ammonium carbonate to pH 7. The product was purified by reverse-phase separation on flash C18 silica gel to give the desired product as proven by MS, $^1$H and $^{13}$C-NMR.

Example 11

Synthesis of Anthrahydroquinone-1,4-diphosphate and naphthohydroquinone-1,4-diphosphate The procedure of Example 10 is performed with the exception of using Anthrahydroquinone or naphthohydroquinone as the starting materials.

Example 12

General Synthesis of Substrate Phosphates: Synthesis of Sesamol Phosphate $POCl_3$ (89.5 mmol) was transferred to a dry 500 ml round bottom flask under a nitrogen atmosphere. A solution of sesamol (35.8 mmol, 1 eq.) and triethylamine (71.7 mmol) in 200 mL of dry dichloromethane was added dropwise over four hours to the POCl₃ solution. After stirring at ambient temperature overnight the solvent was removed by rotary evaporation. The residue was dissolved in 100 mL dichloromethane and the salts removed by filtering through Celite. The product was partitioned into water by quenching with 100 mL saturated ammonium carbonate. The organic layer was discarded and the aqueous phase was dried by rotary evaporation to give 8.2 grams (90% yield) of the desired phosphate. The product identity was confirmed by MS, and analysis by HPLC at 214 nm showed the product to be greater than 99% pure.

Example 13

General Synthesis of Substrate Phosphates: Synthesis of Eugenol and PMCP Phosphates The procedure of Example 12 is performed-with the exception of using eugenol or PMCP (2,2,5,7,8-Pentamethyl-6-chromanol) as the starting materials.

It will be appreciated that the methods and compositions of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalence of the claims are to be embraced within the scope of the invention.

We claim:

1. A method of detecting in situ an immunohistochemical epitope or nucleic acid sequence of interest in a biological sample, comprising:
   binding an enzyme-labeled conjugate molecule to said epitope or sequence of interest;
   contacting said enzyme-labeled conjugate molecule with a redox-inactive reductive species that is a substrate for an enzyme of said enzyme-labeled conjugate and a soluble metal ion, wherein said enzyme is selected from the group consisting of alkaline phosphatase, acid phosphatase, alpha- and beta-galactosidases and esterases; and, wherein the enzyme of said enzyme-labeled conjugate converts said redox-inactive species to a redox-active species that reduces said soluble metal ion to an insoluble metal atom that precipitates at or about the point where said enzyme-labeled conjugate molecule is bound; and,
   detecting in situ said immunohistochemical epitope or nucleic acid sequence of interest in said sample by detecting the presence of said insoluble metal atom precipitated at or about the point where said enzyme-labeled conjugate molecule is bound to said immunohistochemical epitope or nucleic acid sequence.

2. The method of claim 1 wherein said enzyme-labeled conjugate molecule comprises an antibody.

3. The method of claim 1 wherein said enzyme-labeled conjugate molecule comprises a nucleotide sequence.

4. The method of claim 1 wherein said enzyme is alkaline phosphatase, and said substrate is ascorbic acid phosphate.

5. The method of claim 1 wherein said enzyme is alkaline phosphatase, and said substrate is a hydroquinone phosphate.

6. The method of claim 1 wherein said enzyme is selected from the group consisting of alkaline phosphatase and acid phosphatase; and, said redox-inactive reductive species is selected from the group consisting of hydroquinone mono- and di-phosphates, naphthohydroquinone mono- and di-phosphates, and anthrahydroquinone mono- and di-phosphates.

7. The method of claim 1 wherein said enzyme is selected from the group consisting of alkaline phosphatase and acid phosphatase; and, said redox-inactive reductive species is selected from the group consisting of sesamol phosphate, eugenol phosphate and alpha-tocopherol phosphate.

8. The method of claim 1 wherein said soluble metal ion is selected from the group consisting of silver ion and gold ion.

9. The method of claim 1 further comprising pre-treating said biological sample with gold ions and a redox-inactive reductive species after contacting said sample with said enzyme-labeled conjugate but prior to contacting said sample with said soluble metal ion and redox-inactive reductive species wherein said soluble metal ion is silver, and wherein gold particles formed through action of redox active species at or about the point at which said enzyme-labeled conjugate is bound serve as nucleation sites for deposition of metallic silver.

10. The method of claim 1, wherein said enzyme is selected from the group consisting of alkaline phosphatase, acid phosphatase, alpha- and beta-galactosidases, and esterases; and, redox-inactive reductive species that is a substrate for said enzyme has structure (I) below:

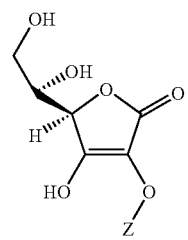

I wherein Z is selected from PO₃²⁻, α-galactose, β-galactose or ester.

11. The method of claim 10, wherein said enzyme is selected from the group consisting of alkaline phosphatase, acid phosphatase and alpha- and beta-galactosidases, and Z is selected from PO₃²⁻, α-galactose or β-galactose.

12. The method of claim 10, wherein said enzyme is selected from the group consisting of alkaline phosphatase and acid phosphatase, and Z is PO₃²⁻.

13. The method of claim 1, wherein said enzyme is selected from the group consisting of alkaline phosphatase, acid phosphatase, alpha- and beta-galactosidases and esterases, and, said redox-inactive reductive species that is a substrate for said enzyme has structure (II) below:

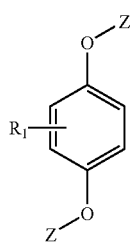

II wherein

R$_1$ is selected from H, alkyl, aryl, carboxylate, carboxyalkyl, NH$_2$, nitro, ether, thioether or sulphonate; and Z is selected from PO$_3^{2-}$, H, α-galactose, β-galactose or ester; but both Zs may not be H.

14. The method of claim 13, wherein said enzyme is selected from the group consisting of alkaline phosphatase, acid phosphatase and alpha- and beta-galactosidases; and, one Z is H and the other is selected from PO$_3^{2-}$, α-galactose or β-galactose; or both Zs are selected from PO$_3^{2-}$, α-galactose or βgalactose.

15. The method of claim 13, wherein said enzyme is selected from the group consisting of alkaline phosphatase and acid phosphatase; and, one Z is H and the other is PO$_3^{2-}$, or both Zs are PO$_3^{2-}$.

16. The method of claim 12, wherein said enzyme is alkaline phosphatase, and, one Z is H and the other Z is PO$_3^{-2}$, or both Zs are PO$_3^{-2}$.

17. The method of claim 1, wherein said enzyme is selected from the group consisting of alkaline phosphatase, acid phosphatase, alpha- and beta-galactosidases and esterases; and, said redox-inactive reductive species that is a substrate for said enzyme has structure (III) below:

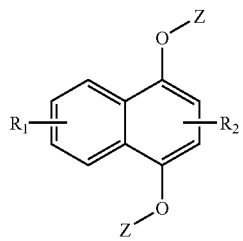

III wherein

R$_1$ is selected from H, alkyl, aryl, carboxylate, carboxyalkyl, NH$_2$, nitro, ether, thioether or sulphonate;

R$_2$ is selected from H, alkyl, aryl, carboxylate, carboxyalkyl, NH$_2$, nitro, ether, thioether or sulphonate; and Z is selected from PO$_3^{2-}$, H, α-galactose, β-galactose or ester; but both Zs may not be H.

18. The method of claim 17, wherein said enzyme is selected from the group consisting of alkaline phosphatase, acid phosphatase and alpha- and beta-galactosidases; and, one Z is H and the other is selected from PO$_3^{2-}$, α-galactose or β-galactose; or both Zs are selected from PO$_3^{2-}$, α-galactose or β-galactose.

19. The method of claim 17, wherein said enzyme is selected from the group consisting of alkaline phosphatase and acid phosphatase; and, one Z is H and the other is PO$_3^{2-}$, or both Zs are PO$_3^{2-}$.

20. The method of claim 17, wherein said enzyme is alkaline phosphatase, and one Z is H and the other Z is PO$_3^{-2}$, or both Zs are PO$_3^{-2}$.

21. The method of claim 1, wherein said enzyme is selected from the group consisting of alkaline phosphatase, acid phosphatase, alpha- and beta galactosidases and esterases; and, said redox-inactive reductive species that is a substrate for said enzyme has structure (IV) below:

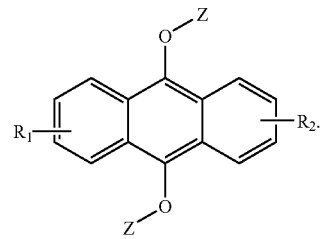

IV wherein

R$_1$ is selected from H, alkyl, aryl, carboxylate, carboxyalkyl, NH$_2$, nitro, ether, thioether or sulphonate;

R$_2$ is selected from H, alkyl, aryl, carboxylate, carboxyalkyl, NH$_2$, nitro, ether, thioether or sulphonate; and Z is selected from PO$_3^{2-}$, H, α-galactose, β-galactose or ester; but both Zs may not be H.

22. The method of claim 21, wherein said enzyme is selected from the group consisting of alkaline phosphatase, acid phosphatase, and alpha- and beta-galactosidases; and, one Z is H and the other is selected from PO$_3^{2-}$, α-galactose or β-galactose; or both Zs are selected from PO$_3^{2-}$, α-galactose or β-galactose.

23. The method of claim 21, wherein said enzyme is selected from the group consisting of alkaline phosphatase and acid phosphatase; and, one Z is H and the other is PO$_3^{2-}$, or both Zs are PO$_3^{2-}$.

24. The method of claim 21, wherein said enzyme is alkaline phosphatase, and one Z is H and the other Z is PO$_3^{-2}$, or both Zs are PO$_3^{-2}$.

25. The method of claim 1, wherein said enzyme is selected from the group consisting of alkaline phosphatase, acid phosphatase, alpha- and beta galactosidases and esterases; and, said redox-inactive reductive species that is a substrate for said enzyme has structure (V) below:

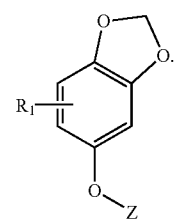

V wherein

R$_1$ is selected from H, alkyl, aryl, carboxylate, carboxyalkyl, NH$_2$, nitro, ether, thioether or sulphonate; and Z is selected from PO$_3^{2-}$, α-galactose, β-galactose or ester.

26. The method of claim 25, wherein said enzyme is selected from the group consisting of alkaline phosphatase, acid phosphatase and alpha- and beta-galactosidases; and Z is selected from PO$_3^{2-}$, α-galactose or β-galactose.

27. The method of claim 25, wherein said enzyme is selected from the group consisting of alkaline phosphatase and acid phosphatase, and Z is PO$_3^{2-}$.

28. The method of claim 25, wherein said enzyme is alkaline phosphatase and Z is PO$_3^{2-}$.

29. The method of claim 1, wherein said enzyme is selected from the group consisting of alkaline phosphatase, acid phosphatase, alpha- and beta galactosidases and esterases; and, said redox-inactive reductive species that is a substrate for said enzyme has structure (VI) below:

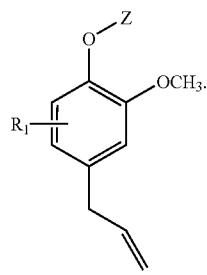

VI wherein
$R_1$ is selected from H, alkyl, aryl, carboxylate, carboxyalkyl, $NH_2$, nitro, ether, thioether or sulphonate; and
Z is selected from $PO_3^{2-}$, α-galactose, β-galactose or ester.

30. The method of claim 29, wherein said enzyme is selected from the group consisting of alkaline phosphatase, acid phosphatase and alpha- and beta-galactosidases; and, Z is selected from $PO_3^{2-}$, α-galactose or β-galactose.

31. The method of claim 29, wherein said enzyme is selected from the group consisting of alkaline phosphatase and acid phosphatase, and Z is $PO_3^{2-}$.

32. The method of claim 29, wherein said enzyme is alkaline phosphatase and Z is $PO_3^{2-}$.

33. The method of claim 1, wherein said enzyme is selected from the group consisting of alkaline phosphatase, acid phosphatase, alpha- and beta galactosidases and esterases; and, redox-inactive reductive species that is a substrate for said enzyme has structure (VII) below:

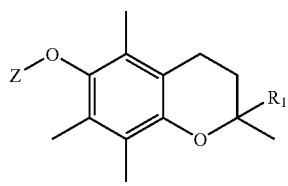

wherein
$R_1$ is selected from H, alkyl, aryl, carboxylate, carboxyalkyl, $NH_2$, nitro, ether, thioether or sulphonate; and
Z is selected from $PO_3^{2-}$, α-galactose, β-galactose or ester.

34. The method of claim 33, wherein said enzyme is selected from the group consisting of alkaline phosphatase, acid phosphatase and alpha- and beta-galactosidases; and, Z is selected from $PO_3^{2-}$, α-galactose or β-galactose.

35. The method of claim 33, wherein said enzyme is selected from the group consisting of alkaline phosphatase and acid phosphatase, and Z is $PO_3^{2-}$.

36. The method of claim 33, wherein said enzyme is alkaline phosphatase and Z is $PO_3^{2-}$.

37. The method of claim 1, wherein said enzyme is alkaline phosphatase.

38. The method of claim 1, wherein said enzyme is acid phosphatase.

39. The method of claim 1, wherein said enzyme is alpha-galactosidase.

40. The method of claim 1, wherein said enzyme is beta-galactosidase.

41. The method of claim 1, wherein said enzyme is esterase.

* * * * *

UNITED STATES PATENT AND TRADEMARK OFFICE
CERTIFICATE OF CORRECTION

| | | |
|---|---|---|
| PATENT NO. | : 7,632,652 B2 | Page 1 of 1 |
| APPLICATION NO. | : 10/877919 | |
| DATED | : December 15, 2009 | |
| INVENTOR(S) | : Bieniarz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1239 days.

Signed and Sealed this

Second Day of November, 2010

David J. Kappos
*Director of the United States Patent and Trademark Office*